United States Patent [19]

Haynes

[11] 4,307,727
[45] Dec. 29, 1981

[54] WRIST BAND TRANSDUCER SUPPORT AND TENSIONING APPARATUS

[75] Inventor: Russell R. Haynes, Morgantown, W. Va.

[73] Assignees: Tech Engineering and Design, Inc., Morgantown, W. Va.; Ronald L. Broadwater, Sr., Timonium, Md.

[21] Appl. No.: 84,947

[22] Filed: Oct. 15, 1979

[51] Int. Cl.³ ............................................... A61B 5/02
[52] U.S. Cl. ..................................... 128/672; 128/690
[58] Field of Search ........................ 128/644, 687–690; 63/5 R, 9; 2/311–312, 317, 319, 325, 337; 24/31 R, 33 R, 31 H, 32

[56] References Cited

U.S. PATENT DOCUMENTS

| 3,426,747 | 2/1969 | Herman et al. ............... 128/690 |
| 3,903,873 | 9/1975 | Royal et al. .................. 128/688 |
| 4,181,134 | 1/1980 | Mason et al. ................. 128/690 |

FOREIGN PATENT DOCUMENTS

| 671279 | 10/1963 | Canada ............................ 128/690 |
| 2637669 | 9/1977 | Fed. Rep. of Germany ...... 128/690 |
| 2751031 | 5/1979 | Fed. Rep. of Germany ...... 128/689 |
| 2224 | of 1865 | United Kingdom ............... 24/32 |

*Primary Examiner*—Robert W. Michell
*Assistant Examiner*—Francis J. Jaworski

*Attorney, Agent, or Firm*—Pollock, Vande Sande & Priddy

[57] ABSTRACT

A digital watch is utilized to measure blood pressure or heart rate by means of a pressure transducer that contacts the wrist adjacent the radial artery of the wrist and generates electrical pulses corresponding to the blood pressure pulses of the radial artery. A support member is pivotally connected at one end to the watch band and the member supports the transducer at its other end. The support member engages a sliding switch in a first position to hold the transducer in contact with the wrist. The switch engages the hinged member in a second position to hold the transducer out of contact with the wrist. A micro switch supplies power to the blood pressure pulse analyzing circuitry of the watch when the transducer contacts the wrist. The tension of the wrist band is adjusted by a housing that connects two ends of the band and that slidably supports a cam follower and rotatably supports a cam. The cam follower has a tab that engages a spiral groove in the cam. When the cam is rotated, the tab of the cam follower moves along the groove and the cam follower is thereby caused to slide in the housing. The sliding movement of the follower in response to the rotation of the cam either shortens or lengthens the band, thereby adjusting the tension of the band with respect to a wearer's wrist and the corresponding contact pressure between the engaged transducer and the wrist.

2 Claims, 5 Drawing Figures

WRIST BAND TRANSDUCER SUPPORT AND TENSIONING APPARATUS

DESCRIPTION

1. Technical Field

The invention relates to electronic watches that are employed to noninvasively measure blood pressure or heart rate and, more particularly, to such watches including a watch band having means for selectively applying a pressure transducer to an area adjacent the radial artery of the wrist and for adjusting the tension of the watch band to adjust the pressure at which the transducer is applied to the wrist.

2. Background Art

Devices that may be strapped to the wrist to measure heart rate are known to the art. Such devices typically press a pressure transducer into contact with an area adjacent the radial artery of the wrist. The transducer senses the blood pressure pulses of the radial artery and generates corresponding electrical signals that are analyzed by electronic circuitry to derive the heart rate. The heart rate is then displayed.

It has also been suggested that a wrist-mounted device may be employed to analyze the systolic peaks and diastolic low points of the blood pressure pulses of the radial artery and to thereby determine the systolic pressure and diastolic pressure within the artery.

For blood pressure measurements and to a lesser extent for heart rate measurements, it is desirable to maintain a particular optimum contact pressure between the transducer and the area of the wrist adjacent the radial artery. The contact pressure should be sufficient to provide a good contact between the artery and the transducer, while not unduly constricting the artery and thereby interfering with the measurement of the blood pressure pulses. Thus, in order to provide a pulse analyzing apparatus that may be used by individuals having different wrist sizes and thicknesses of tissue over the radial artery, it is necessary to provide a simple and reliable means for adjusting the contact pressure of the transducer.

Since the optimum pressure between the transducer and the wrist results in some constriction of the radial artery, it is not possible to comfortably wear a blood pressure and heart rate measuring device for a long period of time if the transducer is continually pressed against the wrist. Thus, if the pulse analyzing apparatus is used for a secondary purpose, for example as a watch, it is necessary to provide a means for easily engaging and disengaging the pressure transducer and the wrist, without removing the watch.

Accordingly, it is an object of the invention to provide a relatively simple and effective apparatus for supporting a pressure transducer on the wrist band of a watch and for engaging and disengaging the transducer and an area adjacent the radial artery of the wrist without removing the watch or interfering with the normal fit of the band on the wrist.

Another object of the invention is to provide such an apparatus that will also operate as a switch responsive to the contact of the transducer and the wrist to turn on electronic circuitry and display devices that are utilized to measure and display blood pressure and heart rate.

A further object of the invention is to provide an apparatus that will quickly and easily adjust the tension of a watch band and thereby adjust the contact pressure between a transducer and an area of the wrist.

These and other objects of the invention will become apparent from a review of the detailed specification which follows and a consideration of the accompanying drawings.

DISCLOSURE OF THE INVENTION

In order to achieve the objects of the invention, the apparatus of the invention includes a band that fits around a wrist and that supports a pressure transducer adjacent the radial artery of the wrist.

The band includes two band segments that are linked by a tension adjustment housing and that are affixed to a casing containing electronic circuitry that is employed to analyze the data signals of the transducer. The housing rotatably supports a cam that has a spiral groove formed in an inwardly facing surface and a slot formed in an outwardly facing surface. A cam follower is slidably supported at one end of the housing and the cam follower is attached to an end of one segment of the wrist band. The end of the other segment of the wrist band is affixed to the opposite end of the housing.

The cam follower has a tab portion that engages the groove of the cam. The outwardly facing slot of the cam may be employed to rotate the cam and, as the cam rotates, the tab of the cam follower travels along a path defined by the spiral groove, thereby causing the cam follower to slide in the housing. The sliding movement of the cam follower within the housing adjusts the length of the attached segment of the band and thereby adjusts the tension of the band and the associated contact pressure between the transducer and the radial artery.

A transducer support member is included to engage and disengage the transducer and the radial artery while the wrist band is maintained in position. The support member is pivotally connected at one end to the wrist band and supports the transducer at the other end.

A positioning switch engages the transducer support member in a first position to hold the transducer adjacent the radial artery and engages the transducer support member in a second position to disengage the transducer and the radial artery.

A micro switch is operated to apply power to at least a portion of the electronic circuitry in the casing when the transducer is held adjacent the radial artery.

BRIEF DESCRIPTION OF THE DRAWINGS

FIG. 1b illustrates the face of the watch of FIG. 1a.

FIG. 2 illustrates a side elevation view of the transducer support and control switch for the watch of FIG. 1a.

FIG. 3 illustrates a side elevation view of a tension adjustment apparatus for the band of the watch of FIG. 1a.

BEST MODE FOR CARRYING OUT THE INVENTION

Figure 1A:
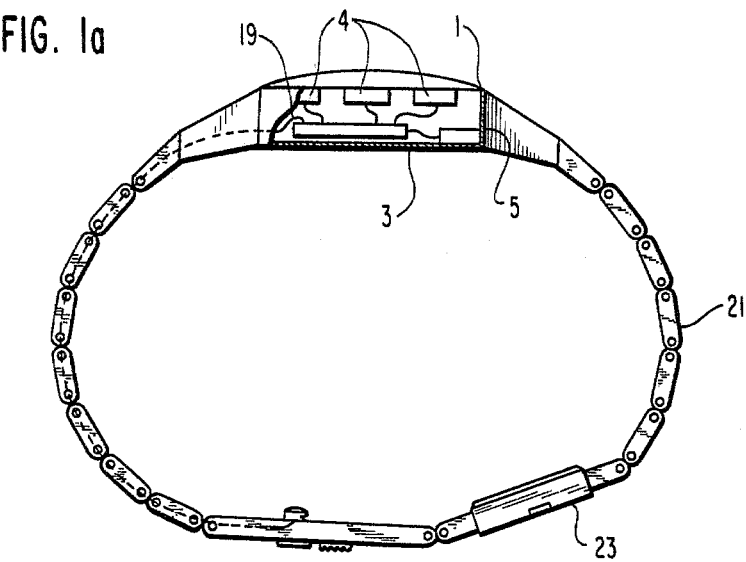
FIG. 1a illustrates a side elevation view in partial section of the heart rate and blood pressure measuring watch in accordance with the invention.

The remaining portion of this specification will describe preferred embodiments of the invention when read in conjunction with the attached drawings, in which like reference characters identify identical apparatus.

FIG. 1a illustrates a side elevation view in partial section of a blood pressure and heart rate measuring watch, in accordance with the invention. A watch case 1 contains electronic circuitry 3 that is employed to register the time and also to generate electrical signals corresponding to the blood pressure and heart rate of the wearer. The watch case 1 also contains a power source, for example a battery 5, that powers the electronic circuitry 3 and associated 7-segment type digital displays 4.

Figure 1B:
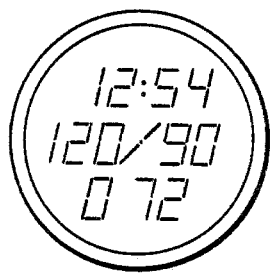

FIG. 1b illustrates the face of the digital display of the watch in accordance with a preferred embodiment of the invention. The topmost portion of the display shows the time in hours and minutes, a middle portion shows the systolic and diastolic pressure separated by a slash mark and the bottom portion of the display shows the heart rate in pulses per minute. It should be appreciated that the display of FIG. 1b may be comprised of either conventional 7-segment light emitting diode elements or liquid crystal display elements. As shown in FIG. 1a, the digital display and associated electronic circuitry and battery are enclosed by a transparent crystal of a known type.

In normal operation, the time measuring circuitry of the watch of FIG. 1a operates in a conventional manner to provide electrical signals corresponding to the time. The watch casing 1 may include a button for selectively activating the time display for a particular period of time, in order to conserve the power of the battery 5. Of course, if the display is a liquid crystal display, the time indication may be continuously shown since very little power is required to operate the display.

Figure 2:
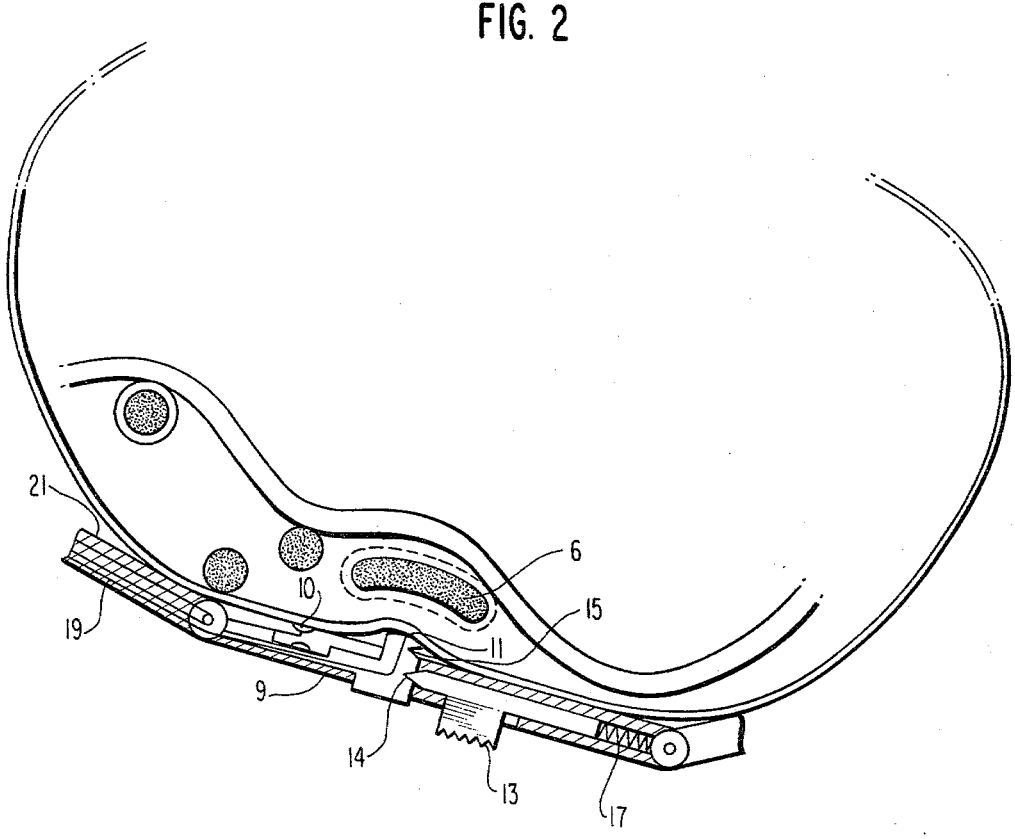

As shown in FIG. 2, the blood pressure and pulse rate circuitry and associated display elements of the watch are activated by pressing inwardly on a hinged transducer support arm 9 having a pressure transducer 11 mounted on an inwardly extending portion of the arm. As the transducer support arm 9 is pressed inwardly, the pressure transducer 11 is forced into contact with the skin of the wrist adjacent the radial artery 6 of the wrist. The inward movement of the support arm activates a micro switch 10 that applies power to the blood pressure and pulse rate circuitry and associated displays over power leads 19 that may be embedded or woven in the material of a watch band 21. A sliding switch 13 is then engaged with an outer notch 14 of the arm 9 so that the transducer 11 is held adjacent the radial artery. The sliding switch 13 is biased by a spring 17 so that the switch will remain in engagement with the outer notch 14 and will thereby maintain the support arm and transducer in an engaged, pressing relation with the radial artery.

As shown in FIG. 1a, the micro switch 10 is deactivated and the blood pressure and pulse rate measuring circuitry and associated displays are thereby de-energized when the transducer 11 is disengaged from the radial artery by moving the support arm 9 outwardly from the wrist and engaging the switch 13 with an inner notch 15. It should be understood that although the watch band 21 of FIG. 1a is shown as a chain-link band, other types of bands may be employed without departing from the spirit of the invention.

The pressure transducer 11 may suitably be comprised of a piezoelectric crystal that generates an electrical signal having a voltage amplitude that corrresponds to the magnitude of applied pressure. Thus, when the heart of the wearer of the watch contracts, a strong pulse of blood is passed through the radial artery, thereby causing the artery to expand and exert a pressure on the piezoelectric pressure transducer 11. The pressure on the piezoelectric transducer will increase to a maximum point, corresponding to the maximum contraction of the heart and, thereafter, the pressue will decrease as the heart expands and the walls of the radial artery contract.

It should be understood that the high internal pressure of the artery at the point of maximum contraction of the heart is the systolic pressure and the lower pressure within the artery at the point of maximum expansion of the heart is the diastolic pressure. Accordingly, the piezoelectric transducer 11 will register an electrical pulse corresponding to each contraction and subsequent expansion of the heart and the voltage at the peak of the electrical pulse will correspond to the systolic pressure, while the low point of the pulse will correspond to the diastolic pressure.

Although a piezoelectric crystal has been utilized as a pressure transducer in a preferred embodiment of the invention, it should be appreciated that other transducers known to the art may be empolyed without departing from the spirit of the invention. However, the piezoelectric transducer is desirable for this application since the transducer measures the direct effect of the pressure exerted within the radial artery, while other transducers, for example resistive strain gauges, measure secondary effects such as the stain forces that are applied at the surface of the skin due to the expansion of the radial artery.

Although there is only a fairly thin layer of tissue covering the radial artery of the average wrist, the force exerted by the radial artery in response to blood pressure pulses is sufficiently small to require that the piezoelectric transducer 11 be held in contact with the wrist at a fairly precise pressure so that the blood pressure pulse is properly registered. In the U.S. patent to Petzke et al, U.S. Pat. No. 3,926,179, it is indicated that blood pressure pulse signals may be maximized by providing a pressure on the radial artery that is sufficient to flatten the artery approximately half-way. In addition to maximizing the blood pressure signals from the artery, the partial flattening of the artery also causes the circumferential tension in the elastic wall of the artery to act in a direction that is perpendicular to the radial pulses of the blood pressure, so that the circumferential tension does not cause inaccuracies in the magnitude of the pulse pressure.

Since individual wrists vary in size and since the skin thickness of wrists also varies, it is necessary to provide a means for adjusting the critical pressure of engagement of the piezoelectric transducer 11 and the radial artery in accordance with the physical characteristics of the wrist of the wearer of the watch. Thus, as shown in FIG. 1a, a tension adjustment apparatus 23 is provided for the wrist band 21 of the watch in order to adjust the size of the band and to thereby adjust the pressure at which the transducer 11 is applied to the radial artery when the sliding switch 13 is engaged with the outer notch 14 of the support arm 9.

Figure 3:
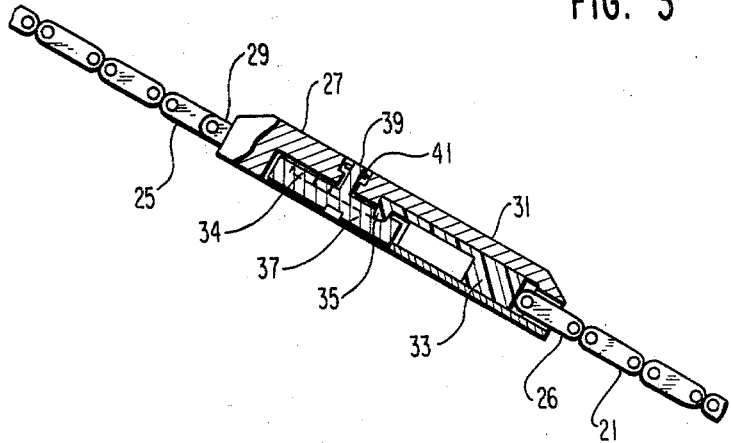
Figure 4:
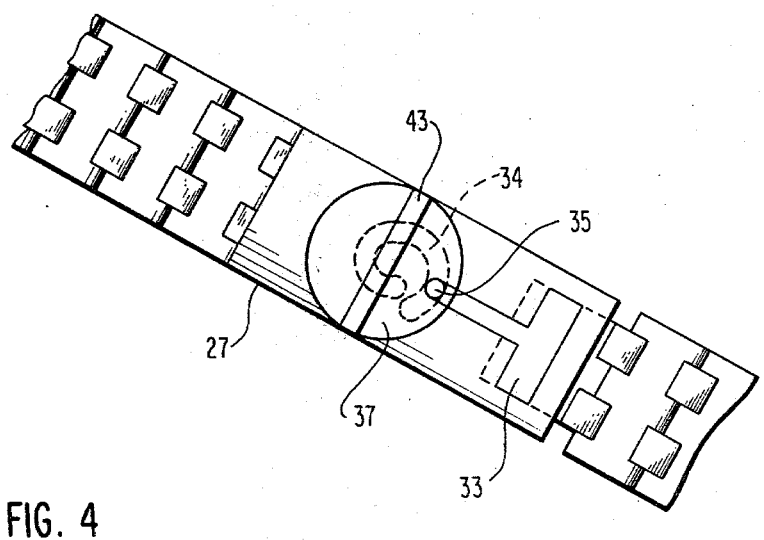
FIG. 4 illustrates a bottom elevation view of the tension adjustment apparatus of FIG. 3.

FIGS. 3 and 4 illustrate a tension adjustment apparatus that may be used to adjust the size of the wrist band 21 in a preferred embodiment of the invention. As shown in FIG. 3, the wrist band 21 may be comprised of links and a connected adjustment housing 27. One end 29 of the adjustment housing 27 is affixed to an end of a link 25 and the opposite end 31 of the adjustment housing 27 is open to admit an associated end link 26 that is affixed to a cam follower 33 that is slidably supported within the adjustment housing. A tab end 35 of the cam follower 33 is engaged with a spiral groove 34 formed in a cam 37 that is mounted for rotation about a shaft 39 within the housing 27. A retainer clip 41 may be affixed at the end of the shaft 39 to hold the cam 37 in a rotatably supported position within the adjustment housing 27.

As shown in FIG. 4, the outward face of the cam 37 has a slot 43 that may be engaged by a screwdriver, coin, or other thin object to rotate the cam 27. It should be understood that as the cam 37 rotates, the tab end 35 of the cam follower 33 will follow the groove 38 in the cam 37 and will thereby cause the cam follower 33 to be slidably moved either inwardly or outwardly with respect to the adjustment housing 27, in accordance with the direction of rotation of the cam 37. Thus, the pressure of engagement of the piezoelectric transducer 11 and the radial artery of the wrist is set by adjusting the tension of the wrist band 21.

It should be appreciated that the tension of the wrist band 21 must be initially adjusted to correspond to the size of a particular person's wrist and the circuitry of the invention must then be calibrated to display proper pressure readings. Of course, a subsequent adjustment must be made if the size of an individual's wrist changes, for example if the individual loses or gains a substantial amount of weight.

The invention may be embodied in other specific forms without departing from its spirit or essential characteristics. The present embodiments are, therefore, to be considered in all respects as illustrative and not restrictive, the scope of the invention being indicated by the claims rather than by the foregoing description and all changes which come within the meaning and range of the equivalents of the claims are therefore intended to be embraced therein.

I claim:

1. In a pulse analyzing apparatus of a type wherein the blood pressure pulses of the radial artery of the wrist are sensed by a transducer and the transducer and an associated casing containing electrical circuit elements are supported by a band fitted around the wrist, the improvement of transducer support apparatus, comprising:

transducer support means pivotally connected at one end to said band and supporting said transducer means at an opposite end;

positioning means for engaging said transducer support means in a first position to hold the transducer in contact with the wrist adjacent the radial artery and for engaging said transducer support means in a second position to disengage the transducer from the wrist; and switch means responsive to the engagement of the transducer with a portion of the wrist adjacent the radial artery for energizing at least a portion of said electrical circuit elements.

2. In a wrist watch of a type wherein a watch casing containing electronic circuit elements and a transducer for measuring blood pressure pulses of the radial artery of the wrist are supported on the wrist by a band fitted around the wrist, the improvement of transducer positioning and tensioning apparatus comprising:

housing means linking a first and a second end of said band, one end of said housing means being affixed to the first end of the band;

cam means rotatably supported in said housing means, the cam means including a curved cam track means and a slot means for rotating the cam means;

cam follower means slidably supported in said housing means and affixed to the second end of the band, the cam follower means having means for engaging the cam track means of said cam means to follow a path defined by the cam track means when the cam means is rotated, the rotation of the cam means causing the cam follower to slide in said housing means to adjust the tension of the band and the contact pressure between the transducer and a portion of the wrist adjacent the radial artery;

transducer support means pivotally connected at one end to said band and supporting said transducer at an opposite end;

positioning means for engaging said transducer support means in a first position to hold the transducer in contact with the wrist adjacent the radial artery and for engaging said transducer support means in a second position to disengage the transducer from the wrist; and switch means responsive to the engagement of the transducer with a portion of the wrist adjacent the radial artery for energizing at least a portion of said electrical circuit elements.

* * * * *